(12) United States Patent
Katzir et al.

(10) Patent No.: US 9,375,027 B2
(45) Date of Patent: Jun. 28, 2016

(54) FRUIT JUICE AND PUREE WITH A LOWERED AMOUNT OF AVAILABLE SUGARS

(75) Inventors: Yuval Katzir, D.N. Hefer (IL); Eli Budman, Moshav Bat Shlomo (IL); Noa Lavid, Kibbutz Hazorea (IL); Yuval Shoham, Haifa (IL); Michael Shemer, Haifa (IL); Ronit Shemer, legal representative, Haifa (IL)

(73) Assignee: Gan Shmuel Foods Ltd., D. N. Hefer (IL)

( * ) Notice: Subject to any disclaimer, the term of this patent is extended or adjusted under 35 U.S.C. 154(b) by 1493 days.

(21) Appl. No.: 12/525,579

(22) PCT Filed: Nov. 19, 2007

(86) PCT No.: PCT/IL2007/001425
§ 371 (c)(1),
(2), (4) Date: Feb. 11, 2010

(87) PCT Pub. No.: WO2008/102336
PCT Pub. Date: Aug. 28, 2008

(65) Prior Publication Data
US 2011/0293782 A1   Dec. 1, 2011

(30) Foreign Application Priority Data
Feb. 19, 2007   (IL) .......................... 181431

(51) Int. Cl.
*A23L 2/02* (2006.01)
*A23L 1/212* (2006.01)
*A23L 1/015* (2006.01)
*A23L 1/307* (2006.01)
*A23L 2/84* (2006.01)

(52) U.S. Cl.
CPC ............. *A23L 1/2128* (2013.01); *A23L 1/0153* (2013.01); *A23L 1/307* (2013.01); *A23L 2/02* (2013.01); *A23L 2/84* (2013.01); *C12Y 204/0101* (2013.01)

(58) Field of Classification Search
USPC ........................... 426/52, 54, 56, 49; 800/284
See application file for complete search history.

(56) References Cited

U.S. PATENT DOCUMENTS

| | | | | |
|---|---|---|---|---|
| 2,680,688 A | * | 6/1954 | Moulton | 426/51 |
| 4,388,330 A | * | 6/1983 | Wobben et al. | 426/51 |
| 5,659,028 A | | 8/1997 | Coussement et al. | |
| 6,147,280 A | * | 11/2000 | Smeekens et al. | 800/284 |
| 6,423,832 B1 | * | 7/2002 | Seljelid | 536/1.11 |
| 6,534,481 B1 | * | 3/2003 | Driguez et al. | 514/25 |
| 6,632,448 B2 | | 10/2003 | Tanaka et al. | |
| 6,635,460 B1 | * | 10/2003 | Van Hijum et al. | 435/193 |
| 6,730,502 B2 | * | 5/2004 | Van Hijum et al. | 435/97 |
| 6,833,491 B2 | * | 12/2004 | Turk et al. | 800/284 |
| 7,608,754 B2 | * | 10/2009 | Weyens et al. | 800/284 |
| 7,803,623 B2 | * | 9/2010 | Caimi et al. | 435/471 |
| 2004/0131659 A1 | * | 7/2004 | Gibson et al. | 424/439 |
| 2009/0221078 A1 | * | 9/2009 | Caimi et al. | 435/471 |
| 2010/0040728 A1 | * | 2/2010 | Henderson et al. | 426/10 |

FOREIGN PATENT DOCUMENTS

WO   WO 2010061383 A1 * 6/2010

OTHER PUBLICATIONS www.http://www.ncbi.nlm.nih.gov/pubmed/19129163 "Structural insights into glycoside hydrolase family 32 and 68 enzymes: functional implications" by Lammens et al. J Exp Bot. 2009;60(3):727-40. doi: 10.1093/jxb/ern333. Epub Jan. 6, 2009.*

* cited by examiner

*Primary Examiner* — Tamra L Dicus
(74) *Attorney, Agent, or Firm* — Roach Brown McCarthy & Gruber, P.C.; Kevin D. McCarthy

(57) ABSTRACT

Fruit juices, purees, and other food products are provided for the healthy-product market. A part of the available sugars in the fruit products is converted to non digestible polymers, thereby lowering the energetic content and simultaneously increasing the nutritional value by forming prebiotic components in the product stables in juices. Further provided is a method of manufacturing juices and purees, enabling to preserve all components but sugars naturally occurring in the fruit.

6 Claims, No Drawings ically present in said fruit; wherein said polysaccharide is at a concentration of at least 10 g/l. The

FRUIT JUICE AND PUREE WITH A LOWERED AMOUNT OF AVAILABLE SUGARS

REFERENCE TO CO-PENDING APPLICATIONS

Priority is claimed from a 371 of international of PCT/IL2007/001425, filed on Nov. 19, 2007; which claims priority from Israeli patent application no. 181431, filed on Feb. 19, 2007.

FIELD OF THE INVENTION

The present invention relates to a process for manufacturing fruit juices and purees with lowered energetic content due to lowered amounts of available sugars, and due to the formation of non digestible carbohydrates, particularly prebiotic polymers, wherein all fruit components except for carbohydrates are essentially maintained in their natural amounts.

BACKGROUND OF THE INVENTION

Obesity is a major public health problem, and about two thirds of the adults in the United States may be overweight, when applying various criteria. The health problems associated with overweight, including type 2 diabetes and cardiovascular diseases to name some, are attributed nearly half a million deaths per year in the USA, and the costs related to overweight may be greater than $100 billion. Treatment of overweight comprises hundreds of diet regimens, and the consumers invest about $30 billion annually on weigh-loss products and services. Lowering daily caloric intake is painful, and the most simple and the least expensive, of course, would be to lower energetic content in the food items in which it is least felt, a good example being a beverage, such as a fruit juice. Even a minor energetic reduction may have a substantial effect when the item in question is consumed in large volumes, the best example being, again, a popular beverage.

Fruit juices have kept their position among the most popular drinks for many years all around the world, 75% of juices consumed in households being orange juices. Oranges, with a yearly production of about 60 million tons, hold a share of nearly one quarter of all fruit produced in the world. For many years, concentrated juice extracts were used, but their sales have declined during last several years due to the increasing popularity of low-carbohydrate and low-caloric diets, and due to the growing demand for what is called healthy and natural products. The orange concentrates may be, for example, five times more concentrated than squeezed juice, making their storage more economical, but health-conscious consumers often prefer not-from-concentrate (NFC) juices, and nondiluted juices. In view of huge and widespread juice consumption, it would be very useful to lower energetic content of the juices, including NFC juices, however small such reduction should be.

Some saccharides, although bearing biochemical energy, cannot be digested in the human alimentary tract, and even though possibly contributing to organoleptic properties of food, they do not contribute to the available energy. Fructose oligomers or polymers, called also fructans, belong among such saccharides; moreover, fructans have been recognized also as prebiotic agents supporting beneficial bacteria such as *Bifidobacteria* and *Lactobacilli*. Fructans are produced by various fructosyltransferases in plants, yeasts, fungi and bacteria, and are usually divided to inulines, that comprise predominantly β(2→1) glycosidic bonds, and levans, that comprise predominantly β(2→6) glycosidic bonds between adjacent fructose units. The potential of fructans for human diet was recognized, for example, in U.S. Pat. No. 4,681,771, that describes enzymatic preparation of a low-calorific fructan-based sweetener from sucrose, and its use in producing sweetened low-calorific food products. U.S. Pat. No. 6,808,703 provides microorganisms to be delivered to the intestines, where they should convert digestible saccharides to indigestible ones, thereby treating obesity and diabetes.

It is an object of this invention to provide a process for manufacturing a fruit juice and fruit puree, comprising reducing the content of metabolically available carbohydrates in the juice or puree.

It is another object of this invention to provide a juice or puree having lowered available sugars, but having other components at their natural concentrations.

It is another object of this invention to provide a process for lowering the caloric content of fruit juice or puree, while upgrading the nutritional value of said juice or puree by forming in them prebiotic components.

Other objects and advantages of present invention will appear as description proceeds.

SUMMARY OF THE INVENTION

The invention relates to fruit products containing at least one polysaccharide with metabolic availability lower than the metabolic availability of naturally occurring saccharides in said fruit, wherein said fruit product may comprise a fruit juice or fruit puree, or other product obtained from whole fruits or peeled fruits by a process comprising squeezing or crushing. Products according to the invention have a reduced content of lower sugars and a higher content of polysaccharides when compared to the raw materials from which they are manufactured. The term "crushing", as used herein, is intended to comprise any disintegrating procedure that provides from the edible parts of the fruit a fluid, a paste, or a suspension of any density or coarseness. Said squeezing or crushing provides a raw fruit material from which the fruit products of the invention are manufactured, wherein said raw materials may have a consistency of juice, suspended pulp, mash, slurry, or puree. In a preferred aspect of the invention, said fruit product has the same consistency as the raw fruit material from which it is produced. In another aspect, the manufacturing procedure comprises steps of adding or removing water, resulting in a changed consistency. A fruit product for use as a beverage is called a juice, whereas all other products are called a puree, for the sake of brevity. Said saccharides with lowered metabolic availability are formed from natural juice sugars in situ in said raw material via an enzymatic process and are not added. Preferably, said fruit product of the invention contains saccharides with lowered metabolic availability at a concentration of at least 10 g/l. The terms saccharide(s) and carbohydrate(s) and sugar(s) are used interchangeably throughout.

The invention provides a fruit juice or puree containing a non-added polysaccharide exhibiting lower metabolic availability than the naturally occurring sugars in said fruit, the polysaccharide being at a concentration of at least 10 g/l. The term polysaccharide as used herein is intended to include saccharides comprising more than ten monosaccharide units in the molecule, whenever not stated otherwise. In a preferred embodiment, the concentrations of naturally occurring components in a fruit juice or puree according to the invention, except for carbohydrates and possibly water, are the same as in an original raw juice or puree, freshly obtained from said fruit; wherein said metabolic availability of said non-added saccharide is lowered relatively to the carbohydrates originally present in said raw juice or puree; and wherein said original raw juice or puree is obtained from said fruit by squeezing or crushing. In preferred products of the invention, the quantities of all naturally occurring components except for carbohydrates are the same as in an original raw juice or puree, freshly obtained from said fruit; wherein said metabolic availability of said non-added saccharide is lowered relatively to the carbohydrates originally present in said raw juice or puree; and wherein said original raw juice or puree is obtained from said fruit by squeezing or crushing.

Said saccharide with lowered metabolic availability is created in the juice of the invention in situ, from one or more naturally occurring saccharides, present in a freshly squeezed raw juice. Said saccharide with lowered metabolic availability is created in the puree of the invention in situ, from one or more naturally occurring saccharides, present in a freshly crushed puree. Said saccharides with lowered metabolic availability are created in situ in the presence of an enzyme exhibiting a glycosyltransferase activity, or other activity enabling restructuring saccharides, such as carbohydrate ligase, glycosyl hydrolase, etc. The juice or puree of the invention preferably does not comprise any added saccharides. However, the juice or puree comprises an added enzyme, in amounts sufficient to achieve the desired sugars conversion within practically acceptable pH, temperature and time periods of industrial production. Said saccharide with lowered metabolic availability may be fructan, said enzyme may be an enzyme exhibiting a fructosyltransferase activity. In a preferred embodiment of the invention, a fruit product contains polyfructan. A preferred glycosyltransferase produces saccharides of at least ten monosaccharide units, and still more preferably polysaccharides consisting of hundreds or more of monosaccharide units. In a preferred process according to the invention, at least by 90% of the enzyme is deactivated after the polysaccharide formation, and nearly no reaction continues during the storage. No polysaccharide hydrolysis should occur during the storage. Said polyfructan is preferably of levan type. A fructan concentration of at least 10 g/l and a sucrose concentration of at most 8 g/l are preferably reached. The term fructan as used herein includes oligofructans and polyfructans. The term oligofructan is intended to include saccharide chains comprising from two to ten fructose units; the term polyfructan includes, whenever not stated otherwise, saccharide chains comprising more than ten fructose units. Preferred embodiments of the instant invention relate to polyfructans consisting of hundreds or thousands of fructose units, linked predominantly by $\beta(2\rightarrow6)$ glycosidic bonds. Said juice product and said raw juice have preferably essentially the same total saccharide contents, and essentially the same contents of other components, naturally occurring in a freshly squeezed juice. Said juice may be a NFC juice. Said fruit juice has lowered amount of metabolically available sugars, when compared to said raw juice, containing 10 g/l or more, and preferably 20 g/l or more fructans. A juice according to the invention is useful in prebiotic diets. The fruit puree according to the invention is in a preferred embodiment a fruit puree having lowered amount of metabolically available sugars, when compared to said raw puree, containing fructans, and being useful in prebiotic diets.

The invention relates to a process for converting starting raw juices or purees into juice products or puree products with lowered energy content. The juices or purees with lowered metabolically available volume energy are further called, for the sake of a simple description, low-erg juices or purees, respectively. The juice or puree manufactured by the method of the invention exhibits a lowered energetic content as a result of less sugars that are metabolically available, although the total sum of all sugars is essentially nearly the same in the juice or puree product as in the raw juice or puree. The invention relates to a process for manufacturing a fruit juice or puree containing a polysaccharide with lowered metabolic availability at a concentration of at least 10 g/l, comprising steps of i) providing a raw fruit juice or puree containing mono- and disaccharides (lower sugars); and ii) contacting said lower sugars with an enzyme capable of converting at least a part of the lower sugars into polysaccharides that are less digestible in the human alimentary tract than said lower sugars. In one embodiment, the process is provided for manufacturing a juice containing saccharides with lowered metabolic availability at a concentration of at least 10 g/l and preferably at least 20 g/l, comprising steps of i) providing a raw fruit juice or puree containing monosaccharides and disaccharides (lower sugars); and ii) introducing into said raw juice or puree an enzyme capable of converting a part of said lower sugars into polysaccharides that are less digestible in the human alimentary tract than said lower sugars. Said polysaccharide may have a molecular weight of at least 20 kDa. Said saccharides with lowered metabolic availability may be, in one embodiment of said process, fructan, mainly polyfructan, essentially levan and said enzyme may exhibit, for example, a fructosyltransferase activity. In one embodiment of the invention, a process for manufacturing a low-erg fruit juice or puree comprises steps of i) providing a raw fruit juice containing monosaccharides and disaccharides (lower sugars); and ii) introducing into said raw juice or puree an enzyme capable of converting a part of said lower sugars into polysaccharides that are less digestible in the human alimentary tract than said lower sugars; thereby the available caloric value of the juice or puree is lowered and said low-erg fruit juice or puree is obtained. Said process for manufacturing a low-erg fruit juice or puree comprises a step of introducing into a raw fruit juice containing sucrose an enzyme capable of converting a part of said sucrose into one or more fructans, thereby lowering the sucrose concentration in the juice or puree to 8 g/l or less, preferably less than 2 g/l. Said juice or puree manufactured by a process according to the invention exhibits a reduced amount of metabolically available sugars, when compared to said raw juice or puree, respectively. In a preferred process of the invention, said juice or puree contains fructan(s) at a concentration of at least 10 g/l, and exhibits reduced energetic content when compared to said raw juice or puree. In one embodiment, the process for manufacturing a low-erg fruit juice of the invention comprises steps of i) providing a raw fruit juice; contacting said raw juice with an enzyme having fructosyltransferase activity, while slowly stirring for a time period sufficient for lowering the sucrose concentration to 8 g/l or less; and heating said juice containing fructan at a temperature of 85-125° C. for a period of time sufficient for pasteurizing the juice and deactivating at least 95% activity of said enzyme; thereby obtaining a juice containing fructan(s), and having a lowered content of metabolically available sugars and metabolically available energy, when compared to said raw juice. In a preferred embodiment of the invention, said raw juice or puree is obtained without a concentrating or a diluting step. In one aspect of the invention, said low-erg juice in the process of the invention may be an NFC juice, and said puree may be a puree processed without dilution or concentration steps. In other aspect of the invention, said low-erg juice in the process of the invention may be selected from diluted juice, concentrated juice, and reconstituted juice; said puree may be a concentrated puree, or reconstituted puree, and otherwise processed non-diluted and non-concentrated puree. In one embodiment of the invention, a process according to the invention comprises steps of i) providing a concentrated juice or a concentrated puree containing lower sugars; introducing into said juice or puree concentrate an enzyme capable of converting at least a part of said lower sugars into polysaccharides that are less digestible in the human alimentary tract than said lower sugars; and diluting the concentrate after the conversion. Said dilution is preferably performed so that the original water content of the raw juice or puree is restored. In an important embodiment of the invention, said enzyme converting the lower sugars into the polysaccharides is added to the raw juice or puree. In other embodiment of the invention, said enzyme converting the lower sugars into the polysaccharides is added to a concentrated or diluted juice or puree. In a still other embodiment of the invention, said process further comprises a step of dilution or concentration of an enzymatically processed juice or puree. Said raw juice may be advantageously a freshly squeezed juice. The total saccharide content of the juice remains essentially unchanged in the process of the invention, and the amounts of other components, naturally occurring in said raw juice, remain essentially unchanged. The available energetic content of the low-erg juice may be lowered by 15-40% in the process of the invention, when compared to the energetic content of said raw juice. Said fruit for manufacturing a juice by the process of the invention may be, for example, selected from orange, apple, pineapple, strawberry, and other fruits, and mixtures thereof. Said fruit for manufacturing a fruit puree by the process of the invention may be, for example, selected from apple, pear, pineapple, peach, apricot, mango, banana, strawberry, and their mixtures.

Said enzyme, assisting in the conversion of the carbohydrates in the process of the invention, may be selected from naturally occurring enzymes, recombinant or modified engineered enzymes. A skilled person will employ the enzyme under such conditions that will allow to reach the desired sugars concentrations, in accordance with known or determined properties of the used enzyme, so that the required temperatures and enzyme concentrations will be selected. For example, an enzyme exhibiting fructosyltransferase activity is added and the incubation may comprise a temperature of from about 0 to about 55° C., a pH range from about 3 to about 7, for a time period sufficient to lower the sucrose concentration to 8 g/l or less; however, the final reaction conditions take into consideration the enzyme activity under different pH, temperatures and sugar concentrations, enzyme stability, juice stability, and other factors associated with the enzyme properties and microbiological evaluations, as well as organoleptic considerations.

Thus, said process comprises enzymatic transformation of sugar molecules, but the total carbohydrates mass remains essentially unchanged. Also essentially unaffected remain other components, naturally occurring in the used fruit and passing to said raw juice or puree. An available energetic content of a fruit juice or puree according to the invention may be lowered by at least 10%, and preferably by more than 25%. Said enzyme may be a natural enzyme, a recombinant enzyme, a modified enzyme with improved stability or an engineered recombinant enzyme with desired properties. The enzyme, converting sucrose to fructans, may be either a free enzyme or an immobilized enzyme. *Zymomonas mobilis* levansucrase was found to be surprisingly convenient for the method of the invention. A fruit juice or puree according to the invention contains metabolically non-available polysaccharides; and the total amount of the non-available polysaccharides is stable and does not change under regular processing and storing conditions; the meaning of the term stable in this context is as explained herein; although certain changes in the structure of said polysaccharides may occur during the storage, such changes will not affect said metabolic availability. In a preferred embodiment of the invention, polysaccharides with lower availability are stable for at least one year under regular processing and storing conditions.

The invention is directed to fruit products for a healthy product market, which contain fructan at a concentration of at least 10 g/l and preferably at least 20 g/l, while having a lowered sucrose concentration, reduced down to 8 g/l or less, preferably less than 2 g/l. The product according to the invention may be prepared from a raw fruit juice or puree without employing any concentrating or diluting steps, or it may be prepared from concentrates and other fruit products. The invention, in one aspect, provides diluted or concentrated products, namely juices and purees.

The invention is, in one aspect, directed to a food product selected from fruit juice or puree containing a polysaccharide formed from lower sugars by an added enzyme, wherein said polysaccharide has metabolic availability in the human alimentary tract lower than saccharose, and wherein its concentration in said food product is at least 10 g/l. Said food product may be selected from juices, purees, syrups, jams, and confitures. The juice, may be, for example, a deionized fruit juice concentrate. The invention is also directed to a process of manufacturing said food products containing a polysaccharide with lowered metabolic availability at a concentration of at least 10 g/l, comprising steps of i) providing a raw material containing mono- and disaccharides (lower sugars); and ii) contacting said lower sugars with an enzyme capable of converting at least a part of the lower sugars into polysaccharides that are less digestible in the human alimentary tract than said lower sugars. Said fruit raw material may include, for example, raw or processed juice or puree, or other sources of lower sugars.

DETAILED DESCRIPTION OF THE INVENTION

It has now been found that a fruit juice, for example pineapple or orange juice, can be processed to lower its metabolically available energy without essentially reducing the initial mass of total carbohydrates, and without changing the masses of naturally occurring components in said fruit juices. Of course, diluting a juice with water would lower available energy per volume, but such treatment, although sometimes employed in the art, negatively modifies the organoleptic properties of the beverage, and delivers less of the useful fruit components. A process according to the invention may provide a juice without substantially changed water activity, total carbohydrate concentration, acids, salts, and vitamins. Although totaling to an essentially unchanged sum, in a method according to the invention, the juice carbohydrates undergo a molecular rearrangement leading to a lowered available energy of the juice. The means for said rearrangement is an enzyme capable to convert a part of the digestible carbohydrates into less digestible or nondigestible carbohydrates. Particularly, the process of the invention comprises enzymatically converting a part of digestible sugars, such as disaccharides, into higher polysaccharides which are less digestible in the human alimentary tract.

In one aspect of the invention, a levansucrase originating from *Zymomonas mobilis* is applied for processing fruit juices and fruit concentrates or purees, reducing the available sugars and energy in the products, and producing prebiotic carbohydrates of high molecular weight. When developing the process of the invention, it was found that cloned and purified *Z. mobilis* levansucrase was able to efficiently convert available sugars to polyfructans under natural juice conditions, namely at pH of 3.5-6.5, and at a temperature of 0-15°

C. Levansucrases of glycosyl hydrolase family (GH68), such as for example *Zymomonas mobilis* levansucrase, classifiable as E.C. 2.4.1.10, provided, under the conditions of the method of the present invention, desired results, contrasting previous controversial and inconsistent published reports; Crittenden and Dolle [Appl. Microbiol. Biotechnol. 41 (1994) 302-8], for example, reported 1-kestose as the major product of the transfructosylation reaction, whereas Song and Rhee [Biotechnology Lett. 16 (1994) 1305-10] found a higher molecular weight product. When developing the instant invention, it was found that a unique fibril multimer structure of *Z. mobilis* levansucrase, self-assembled under low pH and high salt, was associated with high polymerization efficiency, yielding high-molecular weight levan as the only product. It was found that by controlling fibril formation during the purification (1.7 fold purification, <90% activity yield), it was possible to obtain high yield of polyfructans. It is suggested that the presence or absence of the self-assembly structures affects the synthetic abilities of *Z. mobilis* levansucrase. Without wishing to be limited by any mechanistic considerations, it is suggested that the fibril multimer structure of *Zymomonas mobilis* levansucrase is responsible for its polymerization activity. Providentially, said fibril structure is supported under the conditions of many natural juices, the enzyme becoming convenient for the method of the invention. It was found that introducing levansucrase affected various juices so that the sum of sucrose, fructose, and glucose decreased, proportionally decreasing the available energy per juice volume. It was further observed that in various juices, including orange, pineapple, apple, and apricot, the effect of levansucrase resulted in the formation of polysaccharides formerly not present, such as levan. Such polysaccharides, e.g. levan, are known to contribute less or at all to the caloric content of food. Under various conditions of the experiments, the energy content of the juices decreased usually by 15-30%. The term "energy content" relates to the metabolically available energy, and may be calculated from analytically determined concentration values of all the components in the juice, according to the tables of specific energy contents in the art.

Conditions were found, under which the enzymes were capable to utilize sucrose and produce, for example, levan and/or inulin in orange or pineapple juices even in a wide range of sugar concentrations, converting the sucrose nearly completely; for example, sucrose naturally occurring in the raw juice was converted within three to five hours at 15° C., the period getting longer with decreasing temperature. The levansucrases that were used, did not show a decomposing activity on levan as substrate. Anyway, the enzyme is preferably deactivated by short heating, which may be optionally a part of the pasteurization step. The enzyme was used in the reaction mixtures at a concentration ensuring the maximal conversion of sucrose into fructans under original juice pH and acceptable temperature. In bacteria, plants, yeasts and fungi there are other numerous enzymes having fructosyltransferase activity, and capable of producing fructans, i.e. oligosaccharides and polysaccharides in which at least two fructose units are coupled to a glucose unit, which oligosaccharides and polysaccharides are not digestible, even though they may contribute to the organoleptic properties of juices. In a preferred embodiment of the invention, an enzyme is added to a juice or puree, which shows predominantly polymerase activity under the acidic conditions of the natural juices and purees, a preferred example being *Zymomonas mobilis* levansucrase, which provides high-molecular weight polyfructans in high yield which are, in addition, stable even at long storage under the naturally acidic conditions of the fruit products of the invention. *Z. mobilis* levansucrase supports the desired conversion of lower sugars into polyfructans, when having the fibril multimer structure, in contrast to various enzymes that either synthesize only oligofructans, or, even if enabling the polymer formation, finally decompose the polyfructans at some stages of the reaction or of the storage. The instant invention provides a method for manufacturing healthy beverage or food products, the method comprising pasteurization or sterilization at a temperature of from 85° C. to 125° C. At least 90% of the enzymatic activity should be destroyed under said conditions, but without affecting the quality of the carbohydrates, particularly the prebiotic polymers; however, many enzymes unfortunately show hydrolytic activity at some stages of the heating step or during prolonged storage and especially under acidic conditions, not so *Z. mobilis* levansucrase at the fibril multimer structure.

In some experiments, juices produced in Gan Shmuel Food Ltd. were processed according to the invention, comprising a treatment with levansucrase at pH between 3.5-6, brix 8-70, 43-61% sucrose/total sugar, converting sucrose to levan. A skilled person may choose other juices, and also may choose other enzymes that are capable to rearrange the present sugars in such a way that the sum of digestible sugars is reduced, which is usually indicated by the decreasing sum of three carbohydrates, namely sucrose with glucose and fructose, which decrease is easily measured by any of many analytical methods available in the field, and the simultaneous appearing of oligo- and polysaccharides. A skilled person is aware that observing a sucrose reduction without a reduction in the sum of said three sugars and without appearance of oligo- and polysaccharides does not indicate a desired process, but rather a sucrose hydrolysis.

The invention, thus, relates to a method of manufacturing fruit juice with lowered available energy without increasing water activity, and without essentially lowering total sugar concentration, and without lowering the concentrations of other components naturally occurring in said fruit juice, which components may benignly contribute to the diet, and may include salts, fiber-like material (such as pectin), vitamins (such as vitamin C), ions (such as calcium), or other, according to the fruit that is involved. The process of the invention comprises an enzymatic reaction during which a less digestible sugar is formed in a raw juice or puree, while utilizing sucrose. In a preferred embodiment of the invention, a juice is treated with an enzyme comprising a fructosyltransferase activity, such as levansucrase, and a fructan or fructans are formed, while sucrose is consumed. In a preferred process of the invention, the reaction temperature is not higher than 20° C., and is preferably between 5 and 15° C., for example 10° C. A lower temperature reduces the probability of microbial contaminations, and of undesired chemical processes, and is preferred for levan formation, but on the other hand it prolongs the reaction time. An optimization procedure will take into consideration the issue of eventual contaminations, production efficiency, etc. Naturally low pH partially protects the juice, but pasteurization is desirable; 85-125° C. applied for as short time as possible is preferred, for example 1 minute at about 90° C. The process of the invention lowers metabolically available energy in juices having pH of from 2 to 10, Brix of from 4 to 75, and sucrose/sugars ratio of 10 to 80%.

In one aspect, the invention may provide a fruit juice or a fruit puree for the market of healthy foodstuffs, comprising freshly squeezed fruit juice or freshly crushed puree, which is kept during the whole process at temperatures between 5 and 15° C., except for a pasteurization step which preferably does not include a temperature higher than 94° C. Any steps used in the process are preferably optimized so that the naturally occurring components present in the fresh juice or puree are not destroyed, or their concentrations are not otherwise reduced, except for sucrose whose concentration preferably decreases and serves as a substrate for an enzyme used for fructan synthesis. The amount of digestible sugars in a juice according to the invention is lowered by 13-40%, e.g. by 15-35%, when compared with an untreated juice freshly squeezed from the same fruit. The juice contains at least 10 g/l and preferably at least 20 g/l fructans. The formation of polyfructans in the juice or puree during the process according to the invention results in a reduction of available energy, but polyfructan is not a mere neutral byproduct; polyfructan is recognized as a prebiotic polysaccharide, i.e. a carbohydrate that supports the growth of useful intestinal and colonic microorganisms, such as bifidobacteria. Furthermore, prebiotic polysaccharides are supposed to have anticarcinogenic, antimicrobial (against pathogenic microbes), hypolipidemic, and glucose-modulatory activities. They may also have activity in improving mineral absorption and balance, and may have some anti-osteoporotic effects. Moreover, the produced polyfructan is stable in a high acid medium and resistant to pasteurization at high temperatures in contrast to usual oligosaccharides FOS The juice or puree of the invention, therefore, is an ideal product for the healthy-food market, having lowered energy, while keeping naturally occurring components, and acquiring benign properties of prebiotic fructans.

Generally speaking, the invention is directed to food products that have a reduced content of lower sugars and a higher content of non-metabolized polysaccharides when compared to the raw materials from which they are manufactured. In one aspect said food products are products with lowered amount of available sugars selected from fruit juices and fruit purees, or other products obtained from whole fruits or peeled fruits by a process comprising squeezing or crushing. In other aspect said food products are products with lowered amount of available sugars containing whole fruits, fruit components, or concentrated sugar solutions. The products, obtainable by a process according to the invention include juices, purees, syrups, jams, and confiture with reduced quantity of available sugars. In one embodiment of the invention, a process for manufacturing a sugar syrup containing a polysaccharide with reduced metabolic availability, at a concentration of at least 10 g/l, is provided, comprising i) providing a syrup containing lower sugars, and ii) contacting said lower sugars with an enzyme capable of converting at least a part of said lower sugar into polysaccharides less digestible in the human alimentary tract than said lower sugars. In other embodiment of the invention, a process for manufacturing a deionized fruit juice concentrate containing a polysaccharide with reduced metabolic availability, at a concentration of at least 10 g/l, is provided, comprising i) providing a deionized fruit juice concentrate containing lower sugars, and ii) contacting said lower sugars with an enzyme capable of converting at least a part of said lower sugar into polysaccharides less digestible in the human alimentary tract than said lower sugars. In still other embodiment of the invention, a process for manufacturing a jam or a confiture containing a polysaccharide with reduced metabolic availability, at a concentration of at least 10 g/l, is provided, comprising i) providing a nutritionally acceptable raw material containing lower sugars, and ii) contacting said lower sugars with an enzyme capable of converting at least a part of said lower sugar into polysaccharides less digestible in the human alimentary tract than said lower sugars.

The invention will be further described and illustrated in the following examples.

EXAMPLES

General Procedures

Various enzymes were examined for their ability to decompose sucrose and form fructans, while lowering available sugars at pH from about 3 to about 6.5, at a temperature between 0 and 15° C., and in a wide range of sugar concentrations, comprising 8-70 brix, and 10-70% sucrose/total sugars.

When developing the process, various microbial strains, including yeasts and bacteria, were examined as sources of a fructosyltransferase capable of converting a part of digestible sugars in tested juices into a polysaccharide. Several *Lactobacilli* strains were isolated from milk and apple juices, which showed certain sugar polymerizing activities. US 2004/0185537 describes novel proteins from *Lactobacillus reuteri* having fructosyltransferase activity. Various *Lactobacilli* strains have now been screened for good producers of suitable fructosyltransferase enzymes, either for direct use of such strain or for using its gene for further manipulations, and preparation of a recombinant bacteria. The intended properties of a good enzyme will include capability to work in the environment of various juices, comprising pH from about 3 to about 6.5, at a temperature between 0 and 60° C., and in a wide range of sugar concentrations, comprising 8-75 brix, and 10-80% sucrose/total sugars, with a fructan forming activity providing at least 70% or complete conversions of sucrose within acceptable time. Inulinases were also checked, one produced fructan in apple juices at pH of 3-5, but it worked rather at higher than desired temperatures, above 15° C., and showed higher than desired hydrolase activity, both with inulin and levane as substrate.

*Zymomonas mobilis* ATCC 10988 was obtained from ATCC and its levansucrase (accession no. AF081588) was cloned. The oligomeric structure of the enzyme was studied by means of gel filtration and transmission electron microscopy.

Analysis of Sugar Mixtures

Standard model mixtures, as well as juices, comprising fructose, glucose, sucrose, kestose (fructosyl-fructosyl-glucose), nistose (fructosyl-fructosyl-fructosyl-glucose), levans, and inulins were analyzed by chromatographic methods known in the art.

The reaction mixtures were also analyzed by TLC, carried out on silica gel 60 plates (Fluka), using ethyl acetate:methanol:water (7:2:1, by volume) as the developing solvent. The dry TLC plates were sprayed with "yellow spray" (ammonium molybdate and ammonium cerium nitrate in 10% $H_2SO_4$) to visualize spots. The resultant spots were identified by comparison with standards. The fructans structure, formed in sucrose model solutions and juices by said levansucrases, was analyzed by NMR and was identified by comparison with standard levan and inulin. Average molecular size of the formed levan was determined by gel filtration and found to be usually greater than 1000 kDa. Quantitative analysis of the formed levan was performed also by weighing.

Example 1

Reduction of available sugars in sweetie grapefruit juice was performed by the addition of levansucrase enzyme of *Z. mobilis* origin (E.C. 2.4.1.10). A sample of freshly squeezed pasteurized sweetie grapefruit juice, was taken as is (12.5 Brix, pH: 3.49). Half was supplemented with 200 mg levansucrase (Z. mobilis origin) per 1000 ml juice and half was used as a control without further treatment. The samples were incubated at 4° C. and stirred (15 rpm) for 24 hours. At the end of the experiment the samples were frozen at −20° C., and later analyzed. The sugar concentrations were assessed from HPLC peak areas, and qualitative analysis was performed by TLC, showing no fructans in the control treatment. The fructans were analyzed by NMR and identified as levan.

TABLE 1

| Sample | Glucose conc. g/l | Fructose conc. g/l C/E | Sucrose conc. g/l C/E |
|---|---|---|---|
| Control | 18.3 | 18.8 | 65.1 |
| +Enzyme | 54.8 | 28.7 | 0.9 |
| Change | +33.5 | +9.9 | −64.2 (98.6% conversion) |

The enzyme activity lowered the sum of available sugars wherein the decrease in available sugar mass corresponds to a decrease of about 20.5% in the available energy.

Example 2

Available sugars in fruit concentrates were reduced by adding levansucrase of Z. mobilis origin. Samples from orange and pineapple concentrates were taken as is and supplemented with 200 mg levansucrase per 1000 ml concentrate and incubated at 4° C. Samples were taken for sugar determination at the indicated times. Samples from the concentrates without enzyme supplementation kept under the same conditions were used as controls. The sugar concentrations in reconstituted juices from these concentrates were assessed from HPLC peak areas, and qualitative analysis was performed by TLC, showing no fructans in the control treatment. The fructans were analyzed by NMR and identified as levan.

TABLE 2

| Treatment time | Glucose conc. g/l C/E | Fructose conc. g/l C/E | Sucrose conc. g/l C/E |
|---|---|---|---|
| 1 day | 17.2/28.7 | 21.5/25.3 | 56.3/26.7 |
| 21 days | 18.0/38.8 | 22.3/25.3 | 56.2/6.0 |

C-control,
E- enzyme

Brazilian frozen concentrate orange juice, 65.4 brix, pH: 3.95. Table 2 shows sugars content in reconstituted juice made from these concentrates, 11.2 Brix.

TABLE 3

| Treatment time | Glucose conc. g/l C/E | Fructose conc. g/l C/E | Sucrose conc. g/l C/E |
|---|---|---|---|
| 1 day | 24.1/32.3 | 20.9/20.9 | 70.9/43.9 |
| 21 days | 23.9/49.1 | 21.2/22.5 | 69.4/7.0 |

C-control,
E-with enzyme supplementation

Thai frozen concentrate pineapple juice; 60.6 Brix, pH: 3.53. Table 3 shows sugars content in reconstituted juice made from these concentrates, 12.5 Brix.

According to the results after 21 days at 4° C. approx. 90% of the sucrose in the concentrates was conversed. The very slight increase in fructose content indicates that between 90 to 100% of the produced fructose was converted into fructans, corresponds to a decrease of about 31% in the available energy.

Example 3

The stability of fructan produced in orange juice by levansucrase of Z. Mobilis origin was evaluated. Reconstituted orange juice from Brazilian Concentrate Orange Juice, 11.2 Brix, pH: 3.47, was taken as is, supplemented with 200 mg levansucrase per 1000 ml juice and incubated at 4° C. for 3 hours. A sample from the said juice without enzyme supplementation kept under the same conditions was used as control. The samples were pasteurized at 90° C. for 2 minutes, filled hot in glass bottles and cooled under water. The samples were kept at room temperature during 85 days and checked for available sugars. The sugar concentrations were assessed from HPLC peak areas, and qualitative analysis was performed by TLC, showing no fructans in the control treatment. The fructans were further analyzed by NMR and identified as levan. The results confirmed that the content of the available sugars did not change in the treated orange juice stored at room temperature over periods of at least three months.

While this invention has been described in terms of some specific examples, many modifications and variations are possible. It is therefore understood that within the scope of the appended claims, the invention may be realized otherwise than as specifically described.

The invention claimed is:

1. A food product being fruit juice or puree containing a naturally occurring polysaccharide having (a) at least ten monosaccharide units in the molecule and (b) an amount less than a non-added polysaccharide, the non-added polysaccharide at a concentration of at least 10 g/l, said non-added polysaccharide having metabolic availability lower than the naturally occurring sugars in the fruit and being created in situ, in the presence of an added enzyme, from one or more naturally occurring carbohydrates present in a freshly squeezed raw juice or in a freshly crushed puree, said carbohydrates being selected from monosaccharides and disaccharides, said non-added polysaccharide being polyfructan and comprising at least ten monosaccharide units in the molecule, wherein said added enzyme is a levansucrase of glycosyl hydrolase family 68 (GH) and present in the food product.

2. A fruit juice or puree according to claim 1, in which the concentrations of naturally occurring components except for carbohydrates are the same as in an original raw juice or puree, freshly obtained from said fruit; wherein said metabolic availability of said non-added saccharide is lowered relatively to the carbohydrates originally present in said raw juice or puree; and wherein said original raw juice or puree is obtained from said fruit by squeezing or crushing.

3. A fruit juice or puree according to claim 1, wherein said enzyme is *Zymomonas mobilis* levansucrase and synthesizes polyfructans at a pH of from 3.5 to 6.5, and at a temperature of from 0° C. to 15° C.

4. A fruit juice according to claim 1, being a juice selected from the group consisting of diluted juice, concentrated juice, reconstituted juice, and an NFC juice.

5. A fruit juice or puree according to claim 1, being a fruit juice or puree having lowered amount of metabolically available sugars, when compared to said freshly squeezed raw juice and said freshly crushed puree, said product containing polyfructans, and being useful in prebiotic diets.

6. A fruit juice or puree according to claim 1, wherein said polysaccharide has a molecular weight of at least 20 kD.

* * * * *